United States Patent [19]

Rohr et al.

[11] Patent Number: 4,786,332
[45] Date of Patent: Nov. 22, 1988

[54] ALKYL-SUBTITUTED CYCLOHEXYL AND CYCLOHEXENYL CARBOXYLIC ACIDS AS ODORANTS AND FLAVORANTS

[75] Inventors: Martin Rohr, Glan Rock; N. Peter Vallone, Westwood; Cormack Flynn, Ramsey, all of N.J.

[73] Assignee: Givaudan Corporation, Clifton, N.J.

[21] Appl. No.: 822,707

[22] Filed: Jan. 24, 1986

Related U.S. Application Data

[62] Division of Ser. No. 446,933, Dec. 6, 1982, Pat. No. 4,606,925.

[51] Int. Cl.$^4$ ................................................ A24B 3/12
[52] U.S. Cl. ...................................... 131/276; 512/24
[58] Field of Search ............... 131/275, 276; 426/538; 252/522

[56] References Cited

FOREIGN PATENT DOCUMENTS 0057603 10/1942 Netherlands .
1353382 5/1974 United Kingdom .

OTHER PUBLICATIONS

"Tobacco Flavoring for Smoking Products" by Leffingwell et al, p. 11 last item 1972, Winston Salem, N.C.

Chem Abstracts vol. 95, No. 5, 9/1981.
O. G. 3/1905 pp. 186–187.
Furia et al, Fenaroli's Handbook of Flavor Ingredients 2nd Ed. 1975, vol. CRC Press Cleveland U.S., pp. 338–339.
L. N. Mander and L. T. Palmer, Aust. J. Chem. 32, 823 (1979).
Birch et al, Aust. J. Chem. 26, 1363 (1973).
Varo et al, J. Agr. Food-Chem. 18, 239 (1970).
Kayahara et al., J. Org. Chem., 33,4536 (1968).
H. Van Bekkum et al, Recueil 89, 521 (1970).
C.A. 95:138635d (1981).
C.A. 94:168048m (1981).
C.A. 94:168048m (1981).
F. Camps et al., J. Org. Chem. 32, 2563 (1967).
C.A. 54:8714e (1960).
K. Alder et al., Chem. Ber. 86,1364 (1953).
H. Van Bekkum et al, Recueil 81, 833 (1962).

Primary Examiner—V. Millin
Attorney, Agent, or Firm—Robert F. Tavares

[57] ABSTRACT

The present invention discloses fragrance and flavor compositions comprising 4-alkyl substituted cyclohexyl and cyclohex-3-enyl carboxylic acids wherein the 4-alkyl substituent is an ethyl, propyl or butyl group, and methods for preparing same.

20 Claims, No Drawings

ALKYL-SUBTITUTED CYCLOHEXYL AND CYCLOHEXENYL CARBOXYLIC ACIDS AS ODORANTS AND FLAVORANTS

This is a division of application Ser. No. 446,933, filed 12-6-82, now U.S. Pat. No. 4,606,925.

BACKGROUND OF THE INVENTION

Practitioners of the art of perfumery or flavor creation are engaged in combining a number of substances having individual characteristics to produce a blend which as a desired effect on the senses. The art of perfumery is involved almost exclusively with the sense of smell. The art of flavor creation, however, is based on a combination of the senses of taste, smell, and, in many instances, touch in the form of "mouth feel". It is not surprising therefore, that many substances are commonly used by perfumers and flavorists since both practitioners appeal to the sense of smell in their creative effort.

Many materials used by perfumers and flavorists have organoleptic properties which of themselves are not pleasant or attractive, yet are still very useful for the purpose of blending or unifying certain organoleptic characteristics to provide a fragrance or flavor composition which is considered superior, more finished and complete and is more pleasing to the senses than a comparable composition which does not have that material.

For example, perfumers use materials having what is known in the art as "animalic" odors to simulate a quality known as "warmth" in a fragrance composition. This quality of "warmth" is found in many of the natural floral fragrances, especially Jasmin, Narcissus, Tuberose, Gardenia, Lilac and Ylang. In addition, this quality of "warmth" has in the evolution of the art of perfumery become an inherently desirable quality and is often employed in a variety of fragrance types for both men and women.

The most useful and valued of the animalic odor materials such as civet, castoreum and ambergris are derived from animal secretions. Their limited availability and great expense has led to the search and development of products from synthetic or botanical origins which can economically be used to enhance or imitate the effect of these expensive animal derived products.

Similarly, the flavorist is well aware that natural foods contain a number of compounds which contribute subtle effects to the overall sensory perception and which do not themselves demonstrate a flavor which the ordinary person would associate with that particular food. Indeed, many of these compounds when evaluated in concentrated form are actually unpleasant, yet used in dilute form they tend to blend and unify the other flavoring materials and provide nuances which contribute to the overall impression of the natural flavor.

In creating flavors for foodstuffs and/or luxury consumables (tea, tobacco, etc.) the flavoriest is often seeking to duplicate natural flavors and is constantly looking for chemicals which so contribute to the overall impression of the flavor so as to make it more natural. The flavorist refers to such compounds as contributing "naturalness" to the flavor. The flavor notes which are sought to provide this "naturalness" are often those described as fermented, acidic, woody, musty, sweaty, spicy etc. in character.

THE INVENTION

The present invention concerns fragrance and flavor compositions comprising 4-alkyl substituted cyclohexyl and cyclohex-3-enyl carboxylic acids and methods for preparing same. These acids can be represented by formula I

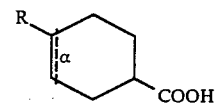

wherein:
the dotted line designated by α represents an optional bond and
R is an ethyl, propyl, or butyl group. Propyl and butyl are to be understood as encompassing both the straight chain and branched isomers.

The compounds of formula I are characterized by organoleptic properties that make them especially useful in fragrance and flavor compositions. Although several of these compounds represented by formula I are known, there is no mention of their organoleptic properties in the prior art.

The compounds of formula I can be prepared by methods similar to those described in the prior art. See L. N. Mander and L. T. Palmer, Aust. J. Chem. 32, 823 (1979) (and references therein); I. N. Nazarov et al., Izvest. Akad. Nauk S.S.S.R., Otdel. Khim. Nauk, 1595 (1959); H. Van Bekkum et al., Recueil 81, 833 (1962); K. Alder et al., Chem. Ber. 86, 1364 (1953); H. Van Bekkum et al., Recueil 89, 521 (1970). A number of preferred methods for their preparation are described herein.

DESCRIPTION OF THE PREFERRED EMBODIMENTS

The 4-alkyl-3-cyclohexene-1-carboxylic acids and the 4-alkylcyclohexane-1-carboxylic acids of formula I have organoleptic properties that make them particularly useful in odorant and flavoring compositions. (See Table I).

TABLE I

| R | α-Bond | Odor Description | Flavor Description |
|---|---|---|---|
| $C_2H_5$ | double | sweaty, intense, fatty, slightly green | woody, fruity, oily, |
| iso-$C_3H_7$ | double | sweaty, intense, fatty, woody | musty, oily, woody |
| n-$C_3H_7$ | double | fatty, sweaty woody | mild, fatty, oily, woody |
| tert-$C_4H_9$ | double | sweaty, waxy, woody | musty, woody |
| $C_2H_5$ | single | green, fatty, woody, earthy | fruity, oily, woody |
| iso-$C_3H_7$ | single | sweaty, oily, weak | weak, woody, spicy |
| n-$C_3H_7$ | single | musty, woody, fatty | mild, weak, spicy, woody |
| tert-$C_4H_9$ | single | weak, fatty, woody | weak, dry, woody |

These organoleptic properties are not of themselves regarded as particularly pleasant or attractive. Their value in flavors and fragrances is not to provide a dominant characteristic, but to provide those subtle characteristics which tend to blend and unify the flavor or fragrance resulting in a more rounded, complete, finished and natural composition.

Those compounds having a perceptably dominant sweaty odor character are considered to be the most valuable for use in fragrance formulations. The 4-alkyl-3-cyclohexene-1-carboxylic acids have this character in a greater degree than their saturated analogs and are preferred for most applications.

Especially preferred for the intense overpowering nature of their perspirative character are those 4-alkyl-3-cyclohexene-1-carboxylic acids in which the alkyl substituent is isopropyl or ethyl, i.e. 4-isopropyl-3-cyclohexene-1-carboxylic acid and 4-ethyl-3-cyclohexene-1-carboxylic acid. The odor of the isopropyl acid is described as intense, sweaty, fatty, woody and is especially preferred for its full-bodied character. The ethyl acid, which is novel, is described as intense, sweaty, fatty, slightly green and is found to have more top note. Both compounds have immense impact in fragrance compositions and can have an effect in some fragrance compositions as low as 0.001%. They are more often used, however, at levels between 0.005 to 0.5%. The odor intensity of these especially preferred compounds is so strong that it is not effectively diminished when used in admixture with formula I compounds of lower intensity. For example, 4-isopropyl-3-cyclohexene-1-carboxylic acid in a mixture containing up to 15% of its saturated analog (4-isopropylcyclohexane-1-carboxylic acid, a compound of low intensity) is found to have an odor impact as effectively penetrating as the essentially pure unsaturated acid. Such mixtures can be used in place of the pure compounds in fragrance compositions and it may be preferred to do so since such mixtures result from a number of the practical synthetic methods described herein.

The 4-alkyl-3-cyclohexene-1-carboxylic acids appear to be stronger, more diffusive, more woody and more spicy than their saturated analogs and are also preferred for use in flavor formulations, foodstuffs and luxury consumables (tobacco, etc.). The 4-isopropyl-3-cyclohexene-1-carboxylic acid is the most effective and is especially preferred.

The compounds of this invention, especially the 4-isopropyl-3-cyclohexene-1-carboxylic acid, appear to have application in a wide variety of flavor types, but are especially useful in highly seasoned foods such as those characterized as Mexican and/or Indian curry type dishes. The use of these compounds tends to blend and unify the various spice notes providing a more blended and natural organoleptic impression.

Similar to the experience found in fragrances, the 4-isopropyl-3-cyclohexene-1-carboxylic acid can be used effectively in admixture with formula I compounds of lower intensity. Since such mixtures result from a number of practical synthetic methods described herein, it is often preferred to use such mixtures.

The 4-alkyl-3-cyclohexene-1-carboxylic acids of formula I can be prepared in a variety of ways, many of which are described or are similar to those described in the prior art. A number of these methods are illustrated below.

CHART I

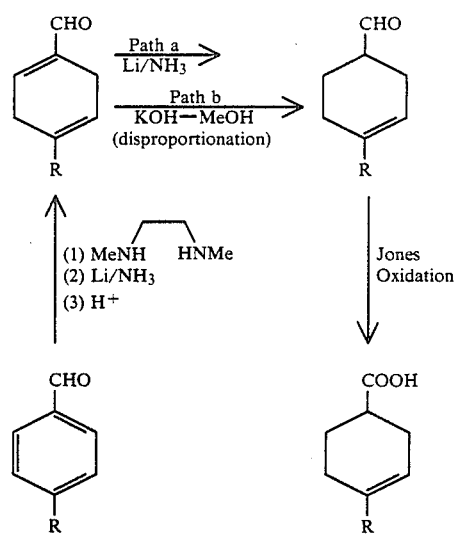

Chart I illustrates a possible general route to the desired acids which utilizes the corresponding 4-alkylbenzaldehydes as starting materials. In accordance with the method of Birch et al. [Aust. J. Chem. 26, 1363 (1973)] the starting benzaldehyde is converted to the 4-alkyl-1,4-cyclohexadiene-1-carboxaldehyde by a Birch reduction of the corresponding N,N'-dimethylimidazolidine followed by acid hydrolysis. The product can then be converted to the desired 4-alkyl-3-cyclohexene-1-carboxaldehyde by a Li/NH$_3$ reduction (path a of Chart I) as described by Mander and Palmer [Aust. J. Chem. 32, 823 (1979)]. It has also been found that the same conversion can be accomplished via a disproportionation reaction (path b of Chart I) which is consistent with the findings of Varo and Heinz [J. Agr. Food Chem. 18, 239 (1970)]. In both instances, the resulting 4-alkyl-3-cyclohexene-1-carboxaldehyde is oxidized to the desired acid, suitably via a Jones oxidation.

The disproportionation reaction (path b of Chart I) is preferably carried out under strongly basic conditions such as in a refluxing solution of potassium hydroxide in methanol. This disporportionation reaction does, however, result in the presence of significant quantities of trans-4-alkylcyclohexane-1-carboxylic acid in the final product (ca. 2-15%). As is clear from this disclosure, the presence of this saturated analog is of little or no consequence since in most instances, and particularly in the case of the 4-isopropyl and 4-ethyl derivatives, the organoleptic characteristics of the mixture are effectively the same as the organoleptic characteristics of the pure unsaturated acid.

While either of the above methods (path a or path b of Chart I) are most suitable as a general synthesis, a specific synthesis has been devised to prepare the 4-isopropyl-3-cyclohexene-1-carboxylic acid whichis preferred for that particular compound. It has been found that perillaldehyde (4-isopropenyl-1-cyclohexene-1-carboxaldehyde) can be converted to the desired 4-isopropyl-3-cyclohexene-1-carboxylic acid in three steps. The first step involves the isomerization of the perillaldehyde to 4-isopropyl-1,3-cyclohexadiene-1-carboxaldehyde. [See H. Kayahara et al., J. Org. Chem. 33, 4536 (1968)]. This compound can then be subjected to a disproportionation step, similar to that shown in path b of Chart I for the 1,4-cyclohexadiene analog, to provide the 4-isopropyl-3-cyclohexene-1-carboxaldehyde which can then be oxidized to the corresponding acid. This process also provides a product containing about 5 to 15% of the corresponding 4-isopropylcyclohexane-1-carboxylic acid (trans-isomer).

Another method, which provides a suitable product in a single step, involves the Birch reduction of the corresponding 4-alkylbenzoic acids. The Birch reduction of 4-isopropylbenzoic acid (cumic acid) as reported does not indicate the formation of the desired 4-isopropyl-3-cyclohexene-1-carboxylic acid. [See F. Camps et al., J. Org. Chem. 32, 2563 (1967)]. It has been found, however, that a product consisting of about 15–20% of the 4-isopropyl-3-cyclohexene-1-carboxylic acid and about 80–85% of the 4-isopropyl-2-cyclohexene-1-carboxylic acid can be prepared by carrying out the reaction in refluxing ammonia (ca.−33° C.) using excess lithium metal (50–100% excess) in the presence of a protein donor such as t-butanol. This mixture of acids exhibits the same odor characteristics as does the pure 4-isopropyl-3-cyclohexene-1-carboxylic acid but has less intensity, the 4-isopropyl-2-cyclohexene-1-carboxylic acid having the effect of a diluent rather than modifying the odor.

To the best of our knowledge, none of the compounds of this invention have been reported to occur in nature. We have, however, found 4-isopropyl-3-cyclohexene-1-carboxylic acid and traces of 4-isopropylcyclohexane-1-carboxylic acid (cis and trans isomers) to be present in commercial cumin oil. It is our view that this acid may not be a constituent of cumin in the natural state, but may be formed by disproportionation and subsequent oxidation of certain cyclohexadiene aldehydes present in cumin.

An alternate way to obtain the 4-isopropyl-3-cyclohexene-1-carboxylic acid would be to extract it from commercial cumin oil per se or to subject the oil to a disproportionation, oxidation procedure (path b, Chart I) and obtain the acid therefrom. The claims should be understood to encompass the use of products obtained in this way. The claims are to be understood as not encompassing the use of commercial cumin oil or any other material derived from nature which may inherently contain an acid of this invention in admixture with the many other compounds of said natural material and which has not been processed for the purpose of increasing the content of the acids of this invention to a point where the processed material can be used as a substitute for said acids contained therein.

The 4-alkylcyclohexane-1-carboxylic acids of this invention can be prepared from their unsaturated analogs by any suitable hydrogenation procedure, many of which are known in the art. For example, procedures known in the art for reducing benzoic acids to the corresponding cyclohexyl acids would be suitable. Such reductions are preferably carried out via catalytic hydrogenation using a rhodium catalyst (e.g. 5% rhodium on alumina), preferably in a solvent (e.g. ethanol containing a small amount of acetic acid). This reaction can be carried out at room temperature and at moderate pressures (about 50 psi). Such reductions of the aromatic ring usually lead to cis, trans isomeric mixtures in which the cis isomer predominates.

The 4-alkylcyclohexane-1-carboxylic acids can also be prepared from the corresponding 4-alkyl-3-cyclohexene-1-carboxylic acids described earlier via a suitable catalytic hydrogenation. Hydrogenation procedures are well known in the art for reducing double bonds in cyclohexene rings. Preferred procedures employ palladium catalysts in hydroxylic solvents. For example, the use of a catalytic amount of 5% palladium on carbon in methanol at room temperature and moderate pressures (about 50 psi) provides the desired saturated acids in good yield. Catalytic hydrogenations using palladium catalysts usually provide isomeric mixtures in which the trans isomer predominates.

From the above it is clear that isomeric mixtures wherein the cis or the trans isomers predominate are easily attainable. Isomer ratios wherein the cis to trans ratio varied from 1:4 to 4:1 were found to have similar odor characteristics.

As mentioned earlier, the 4-isopropyl-3-cyclohexene-1-carboxylic acid and the 4-ethyl-3-cyclohexene-1-carboxylic acid are especially preferred for use in fragrance compositions due to the intense, overpowering nature of their "animalic" odor character. These compounds are several times more intense than the other compounds of formula I. Their odor character is so intense that they have enormous impact even when used in fragrance compositions in concentrations as low as 0.01% to 0.05% of the total base. The presence of other isomers such as the corresponding saturated 4-alkylcyclohexane-1-carboxylic acid or the 4-alkyl-2-cyclohexene-1-carboxylic acid in substantial amounts does not alter the effectiveness of these compounds and such mixtures can be used in place of the pure isomers where desirable with, perhaps, a slight adjustment of the amount used.

While the other compounds of formula I can be used to good effect in perfume formulations, it is the 4-isopropyl-3-cyclohexene-1-carboxylic acid and the 4-ethyl-3-cyclohexene-1-carboxylic acid that were found to be superior as high impact chemicals of an animalic nature. Their use is further illustrated in the examples.

For example, in the creation of an animalic accord, the 4-isopropyl-3-cyclohexene-1-carboxylic acid enveloped and blended the various animalic notes into a unified and pleasingly warm accord. Without the compound, the accord was found to lack sufficient warmth and to be disharmonious in nature and crude and unpleasant in odor, particularly due to the odor of Skatole which stood out. Similar effects can be obtained using the 4-ethyl-3-cyclohexene-1-carboxylic acid.

Similarly, the examples show the beneficial effect of these compounds on a wood base and a musk fragrance. The bases without the claimed 4-isopropyl-3-cyclohexene-1-carboxylic acid were incomplete having odor components that "stood out". The wood base had fatty, earthy and camphoraceous odors that were not in harmony with the desired woody character. The addition of 4-isopropyl-3-cyclohexene-1-carboxylic acid blended these notes to give a warmer, attractive and harmonious woody bouquet. In the musk fragrance without the 4-isopropyl-3-cyclohexene-1-carboxylic acid, the odors of Cedarleaf, Patchouly and Skatole were not fully integrated into the fragrance. The addition of the preferred compound warmed and unified the musky fragrance, while increasing the intensity of impact of its musk character. Again, similar effects can be obtained with the ethyl analog.

The ability of 4-isopropyl-3-cyclohexene-1-carboxylic acid to add a blending or unifying warmth to a fragrance composition was further demonstrated by use in a floral-fruity base and a spice accord. "Warmth" is an important quality in the bouquet of many floral compositions, associated with their "naturalness". In a floral base, in the direction of fruity, odors that were perceived to be harsh and fatty conflicted with the desirable fruity and floral odors and imparted a synthetic quality to the fragrance. The addition of 4-isopropyl-3-cyclohexene-1-carboxylic acid added the necessary warmth that suppressed the harsh fatty odors resulting in a more natural appearing and more desirable floral-fruity fragrance. Similarly, in a spice accord, odor notes were found to be in conflict; the spicy note of Bay oil conflicting with the herbaceous notes of Caraway oil. The addition of the preferred compound produced a warm effect that blended these divergent notes and enhanced the inherent spicy character of the accord.

Depending on the fragrance composition and the compound used, concentrations as low as 0.001% can be used for the more intense 4-isopropyl-3-cyclohexene-1-carboxylic acid and 4-ethyl-3-cyclohexene-1-carboxylic acid. A preferred range for these more intense compounds would be from 0.005% to 0.5% with a range of 0.01% to 0.05% being especially preferred. The less intense compounds would be used in proportionally higher amounts to achieve similar effects, preferably in a range of 0.1 to 1.0%. All of the compounds of formula I can be used at concentrations up to 10% or even higher to produce special effects, the use and effects achieved being limited only by the imagination and ability of the perfumer.

Fragrance compositions containing the compounds of the invention can be used as odorant bases for the preparation of perfume and toilet waters by adding the usual alcoholic and aqueous diluents thereto. Approximately 15–20% by weight of base would be used for perfumes and approximately 3–5% by weight would be used for toilet waters.

Similarly, the fragrance compositions can be used to odorize soaps, detergents, cosmetics, or the like. In these instances, a base concentration of from about 0.5% to about 2% by weight can be used.

As mentioned previously, the 4-alkyl-3-cyclohexene-1-carboxylic acids appear to be stronger, more diffusive, more woody and more spicy then their saturated analogs. They are preferred for use as flavorants for blending and unifying the various components of a flavor composition, for adding "impact" and for adding a quality of naturalness to the flavor. Of the unsaturated acids, the 4-isopropyl-3-cyclohexene-1-carboxylic acid has the best balance of flavor characteristics and is especially preferred for use in flavor compositions.

The ability of the compounds of formula I to add subtle effects to flavor compositions make these compounds useful in a wide variety of flavor compositions and/or foodstuffs, drinks and luxury consumables (i.e. tobacco products, teas, spices etc). These include, but are not limited to spices, salad dressings, meats, gravies, sauces, vegetables, seasonings, seasoned batter mixes for meat dishes, soup mixes, seasoned bread crumbs, cocktail sauces, pizza sauces, spaghetti sauces, vegetable juices, carbonated and non-carbonated drinks, snack foods, teas, tobacco products and the like.

While useful for flavoring a wide variety of products, the compounds of this invention are particularly useful in products wherein a woody or spicy character is desired. Utility in a "woody" type composition is illustrated in the examples by incorporating 4-isopropyl-3-cyclohexene-1-carboxylic acid in an artificial vanilla flavor. The acid had the effect of providing strength and "naturalness" to the flavor and making it more reminiscent of a natural vanilla extract. Other "woody" type compositions wherein the compounds of this invention would be expected to be particularly useful would be blackberry, raspberry, grape, citrus, black pepper, mint, nut, saffron and tobacco flavorings.

Utility in s a spicy type application is demonstrated in the examples by adding 4-isopropyl-3-cyclohexene-1carboxylic acid to a commercial mixed vegetable juice, tomato soup and a seafood cocktail sauce. Each of the products were found to have greater flavor strength, to be spicier and have more "bite" with the acid present.

Utility in a highly seasoned foods of the Mexican or Indian curry type is illustrated in the examples by preparing an artificial cumin flavor (cumin is a constituent in curry powder and finds use in flavoring a number of highly seasoned foods). Two artificial cumin flavor compositions were prepared, the only difference being that one had a small amount of 4-isopropyl-3-cyclohexene-1-carboxylic acid and the other did not. The composition without the acid was found to be flat, thin in body and lacking in impact when compared to the composition that had the acid. The presence of the acid had the effect of rounding out the character of the composition, adding impact or "bite" and creating a more natural character. Subsequent use of these two flavor compositions in a chili receipe even more dramatically demonstrated the effect of the presence of the acid. The chili preparation containing the flavor composition with the acid was stronger, better blended and more full bodied in flavor.

Utility in luxury consumables such as tobacco is illustrated in the examples by adding the 4-isopropyl-3-cyclohexene-1-carboxylic acid to cigarette tobacco. The addition of about 12 ppm of the acid to the tobacco improved the flavor of the tobacco on smoking and the cigarette was found to have a smoother taste with excellent mouth feel and an increased sensation of moistness in the mouth.

As illustrated above, the acids of this invention can be added to foodstuffs, drinks and/or luxury consumables per se or they can be used to prepare flavoring compositions which are to be added thereto. A flavoring composition is comprised of a mixture of flavor imparting substances and perhaps a diluent, carrier and/or other adjuvants. These flavoring mixtures are then used to impart flavors to foodstuffs. Depending on the acid to be used, the flavor desired and the foodstuff to be flavored, the amount of the acid of formula I used in the flavor composition can vary over a wide range. The compounds of formula I may be as little as 0.001% of the flavor imparting substances present. In most applications, however, the acid would be at a level of about 0.005% to 1.0% of the flavor imparting substances present. Levels as high as 10% may be desirable in some applications and, as has been illustrated above, the acid itself may be added to foodstuffs to improve, enhance and/or alter the flavor.

The flavoring substances described above are added to or incorporated into the foodstuffs to be flavored using methods well known in the art. The amount of flavoring composition used will depend on the flavor to be imparted and the foodstuff flavored. The amount of the compounds of formula I used in the foodstuffs can be as little as 0.1 parts per billion to as much as 100 parts per million. In most foodstuffs the level of acid used will be in the range of about 0.01 parts per million to about 100 parts per million.

ILLUSTRATION OF THE PREFERRED EMBODIMENTS

The following examples are provided to illustrate further the practice of the present invention, and should not be construed as limiting.

Gas liquid chromatography was used to analyze the products.

EXAMPLE I

Preparation of 4-Alkyl-3-Cyclohexene-1-Carboxylic Acids

A. 4-Isopropyl-3-Cyclohexene-1-Carboxylic Acid

The 4-isopropyl-3-cyclohexene-1-carboxylic acid was prepared by the following methods:

1. Perillaldehyde as starting material.

A mixture of perillaldehyde (500 g) and 10% sulfuric acid (3 liters) was vigorously stirred for 3 hrs. at reflux (105° C.) under a nitrogen atmosphere. After cooling, the oily layer was separated from the acid, added to methanol (3 liters) and the resultant solution purged with nitrogen. Potassium hydroxide pellets (80 g) were fed into the solution, which was then refluxed (65° C.) for 2 hrs. under an atmosphere of nitrogen. The reaction mixture was then cooled to room temperature and concentrated to 1 liter. The concentrate was diluted with water (3 liters) and extracted with $CH_2Cl_2$ (1.5 liters). The extract was washed neutral with water and concentrated to 490 g of an oil which on distillation yielded 100 g of aldehydes; b.p. 65°–78° C. @ 3.5 mm; analysis: 62% 4-isopropyl-3-cyclohexene-1-carboxaldehyde and 7% trans-4-isopropylcyclohexane-1-carboxaldehyde. A solution was made of the aldehyde mixture in acetone (1 liter) and cooled to 10° C. Jones reagent was prepared from 57.5 ml conc. sulfuric acid, 250 ml water and 66.8 g of chromium (VI) oxide. The reagent (200 ml) was added to the solution at 10° C. over a period of 30 minutes. After an additional 15 minutes at 10° C. the acetone was removed by decantation and the residual chromium salts were washed with additional 200 ml acetone. The combined-acetone solution was concentrated to 500 ml, diluted with 5% aqueous sodium hydroxide (1 liter) and washed with $CH_2Cl_2$ (1 liter). The aqueous phase was acidified with 10% sulfuric acid (1 liter) and extracted with $CH_2Cl_2$. Concentration of the $CH_2Cl_2$ solution yielded a solid (70 g) which on crystallization from hexane (−70° C.) yielded 63 g of a crystalline material; m.p. 58°–60° C.; analysis: (CW 20M fused silica column, 190° C.) 87% 4-isopropyl-3-cyclohexene-1-carboxylic acid and 11% trans-4-isopropylcyclohexane-1-carboxylic acid.

2. p-Isopropylbenzaldehyde as starting material

The method of Mander and Palmer, Aust. J. Chem. 32, 823 (1979) was followed; analysis: 99+% 4-isopropyl-3-cyclohexene-1-carboxylic acid; m.p. 59°–60° C.

3. p-Isopropylbenzoic acid as starting material

To a mixture of p-isopropylbenzoic acid (20 g), t-butanol (100 ml) and liquid ammonia (500 ml) was added lithium (8 g) in small pieces over a period of 2 hrs at reflux (−33° C.). Reflux was continued for 1 hr (total reaction time: 3 hrs) followed by quenching with methanol (250 ml). The ammonia was removed, the residue taken up in water, the solution acidified with diluted sulfuric acid and the product extracted into $CH_2Cl_2$. Drying, filtration and concentration gave 22 g of a crude oil which was distilled through a short Vigreux column to give 16 g of a colorless liquid; b.p. 104°–105° C. @ 0.2 mm; analysis: (CW 20M fused silica column, 180° C.) 16% 4-isopropyl-3-cyclohexene-1-carboxylic acid and 75% 4-isopropyl-2-cyclohexene-1-carboxylic acid.

4. Commercial cumin oil as starting material

Commercial cumin oil (100 g) in methanol (750 ml) was refluxed for 2 hrs under nitrogen in the presence of 15 g of potassium hydroxide. Methanol (500 ml) was removed and water (1 liter) was added. The later mixture was treated in the same manner as that described in part 1. Distillation yielded 19.1 g of material; b.p. 99°–107° C. at 10 mm Hg; analysis: 16% 4-isopropyl-3-cyclohexene-1-carboxaldehyde. The distillate was dissolved in acetone (150 ml) and oxidized with Jones reagent (10 ml) in the same manner as that described in part 1. Crystallization from hexane yielded 3.5 g of product; analysis: (CW 20M fused silica column, 190° C.) 82% 4-isopropyl-3-cyclohexene-1-carboxylic acid, 9% trans-4-isopropylcyclohexane-1-carboxylic acid and 6.7% p-isopropylbenzoic acid.

B. 4-Ethyl-3-Cyclohexene-1-Carboxylic Acid

The 4-ethyl-3-cyclohexene-1-carboxylic acid was prepared from p-ethylbenzaldehyde by the following methods:

1. 4-Ethyl-1,4-cyclohexadiene-1-carboxaldehyde, prepared by the procedure of A. J. Birch and K. P. Dastur, Aust. J. Chem. 26, 1363 (1973) was subjected to the disproportionation and then the Jones oxidation of Section A, part 1. The resultant carboxylic acid was analyzed as follows: m.p. 35°–40° C.; 95% 4-ethyl-3-cyclohexene-1-carboxylic acid and 2.5% trans-4-ethylcyclohexane-1-carboxylic acid.

2. The method of Mander and Palmer was used; see Section A, part 2. Analysis: 99+% 4-ethyl-3-cyclohexene-1-carboxylic acid; m.p. 42°–43° C.

C. 4-n-Propyl-3-Cyclohexene-1-Carboxylic Acid

This compound was prepared from p-n-propylbenzaldehyde employing the method of Mander and Palmer; see Section A, part 2. Analysis: 99+%; m.p. 64°–65° C.

D. 4-t-Butyl-3-Cyclohexene-1-Carboxylic Acid

This compound was prepared from p-t-butylbenzaldehyde by the sequence described in Section B, part 1. Analysis: 95% 4-t-butyl-3-cyclohexene-1-carboxylic acid and 3% trans-4-t-butylcyclohexane-1-carboxylic acid; m.p. 141°–143° C.

EXAMPLE II

Preparation of 4-Alkylcyclohexane-1-Carboxylic Acids

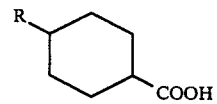

General Procedures:

A. The appropriate 4-alkylbenzoic acid (0.1 mole) in ethanol (100 ml) and acetic acid (0.5 ml) was hydrogenated at 50 psi at room temperature in the presence of 5% rhodium on alumina (1 g) using a Parr shaker.

B. The appropriate 4-alkyl-3-cyclohexene-1-carboxylic acid (0.03 mole) in methanol (150 ml) was hydrogenated at 50 psi at room temperature in the presence of 5% palladium on carbon (0.2 g) using a Parr shaker.

| R | Procedure | cis:trans | MP/BP °C. at mm Hg | Odor |
|---|---|---|---|---|
| C$_2$H$_5$ | A | 3:1 | BP 110° @ 0.5 mm | Green, fatty, earthy, woody |
| iso-C$_3$H$_7$ | A | 3:1 | BP 95° @ 0.1 mm | Sweaty, oily, weak |
| iso-C$_3$H$_7$ | B | 1:3 | MP 45–60° C. | Sweaty, oily, weak |
| n-C$_3$H$_7$ | A | 4:1 | BP 110° @ 0.5 mm | Musty, woody, fatty |
| t-C$_4$H$_9$ | A | 4:1 | MP 93–100° C. | Weak, fatty, woody |

EXAMPLE III

Use of 4-Isopropyl-3-Cyclohexene-1-Carboxylic Acid in Fragrance Compositions

In the following compositions, the acid was used in the form of a 1% solution in dipropylene glycol.

A. Animalic Base

| Constituent | Parts by Weight |
|---|---|
| Isobutyl Linalool | 500 |
| Skatole @ 1% solution in Diproylene Glycol | 10 |
| Phenylacetic Acid | 10 |
| Paracresol @ 10% solution in Dipropylene Glycol | 5 |
| Paracresyl Phenylacetate | 5 |
| Ethylene Brassylate | 250 |
| Sandalore ® [5-(2,2,3-trimethylcyclopent-3-en-1-yl)3-methylpentan-2-ol] | 100 |
| Clove Bud USP | 50 |
| Dipropylene Glycol | 20 |
| Total | 950 |

The above animalic base lacks sufficient warmth and harmony. The odor of the Skatole is not well integrated into the fragrance resulting in a crude and unpleasant odor.

When 50 parts of the 1.0% solution of 4-isopropyl-3-cyclohexene-1-carboxylic acid (0.05%) is added to the base, the various animalic notes of the accord are enveloped and blended into a unified and more pleasing, warm odor.

Similar effects can be achieved by using a like amount of 4-ethyl-3-cyclohexene-1-carboxylic acid.

B. Spice Accord

| Constituent | Parts by Weight |
|---|---|
| Benzyl Salicylate | 938 |
| Bay Oil | 25 |
| 8-Mercapto-p-methane | 7 |
| Caraway Oil | 15 |
| Total | 985 |

The above spice accord lacks warmth and unity. The spicy odor of the Bay Oil does not blend harmoniously with the herbaceous odor of the Caraway Oil.

The addition of 15 parts of the 1% solution of 4-isopropyl-3-cyclohexene-1-carboxylic acid (0.015%) produces a warm effect which blends the discordant notes of the Caraway and Bay Oils, while enhancing the spicy character of the accord.

Similar effects can be achieved by using a like amount of 4-ethyl-3-cyclohexene-1-carboxylic acid.

C. Floral-Fruity Base

| Constituent | Parts by Weight |
|---|---|
| Hydroxycitronellal | 100 |
| Linalool | 200 |
| Benzyl Acetate | 100 |
| Amyl Cinnamic Aldehyde | 200 |
| Benzyl Salicylate | 200 |
| Cinnamic Alcohol | 100 |
| Aldehyde C-16 (Ethyl Phenyl Glycidate) | 3 |
| Gamma Octalactone | 3 |
| Gamma Undecalactone | 3 |
| Dipropylene Glycol | 71 |
| Total | 980 |

In the above floral-fruity composition, undesirable harsh, fatty odors are perceived to be in conflict with the desirable fruity and floral odors of the composition, imparting an undesirable synthetic quality to the fragrance.

The addition of 20 parts of the 1.0% solution of 4-isopropyl-3-cyclohexene-1-carboxylic acid (0.02%) adds a warmth to the composition that suppresses the harsh and fatty odors, blending the whole into a more natural fragrance.

Similar effects can be achieved by using a like amount of 4-ethyl-3-cyclohexene-1-carboxylic acid.

D. Wood Base

| Constituent | Parts by Weight |
|---|---|
| Cedarwood American | 300 |
| Amyris Oil | 300 |
| Vetiver Haiti | 100 |
| Patchouly Oil | 300 |
| Total | 1,000 |

The constituents of the above wood base contribute fatty, earthy and comphoraceous odors that are perceived to be in conflict with the desired woody odor of the base.

The addition of 50 parts of the 1.0% solution of 4-isopropyl-3-cyclohexene-1-carboxylic acid (0.05%) blends the individual odors of the composition to give a warm, attractive and harmonious woody bouquet.

Similar effects can be achieved by using a like amount of 4-ethyl-3-cyclohexene-1-carboxylic acid.

E. Musk Fragrance

| Constituent | Parts by Weight |
|---|---|
| Cedarleaf American | 35 |
| Clove Bud USP | 50 |
| Ethylene Brassylate | 400 |
| Skatole @ 0.1% solution in Dipropylene Glycol | 20 |
| Phenylacetic Acid | 2 |
| Paracresyl Phenylacetate | 2 |
| Patchouly Oil | 30 |
| Sandalore ® [5-(2,3,3-trimethylcyclopent-3- | 15 |

| Constituent | Parts by Weight |
|---|---|
| en-1-yl)-3-methylpentan-2-ol] | |
| Sandela ® NP (isocamphyl cyclohexanols) | 100 |
| Vanillin | 2 |
| Labdanum Soluble Resin | 7 |
| α-Iso-Methyl Ionone | 100 |
| α-Hexylcinnamic Aldehyde | 100 |
| Geranium Oil Bourbon | 15 |
| Benzyl Salicylate | 100 |
| Cinnamon Leaf Ceylon | 2 |
| Total | 980 |

In the above musk fragrance the odors of Cedarleaf, Patchouly and Skatole are perceived to "stand out" from the composition which in itself is found to lack sufficient warmth.

The addition of 20 parts of the 1.0% solution of 4-isopropyl-3-cyclohexene-1-carboxylic acid (0.02%) integrates the discordant notes into the fragrance, creating a warmer and more unified blend of enhanced musky odor and increased intensity.

Similar effects can be achieved by using a like amount of 4-ethyl-3-cyclohexene-1-carboxylic acid.

EXAMPLE IV

Use of 4-Isopropyl-3-Cyclohexene-1-Carboxylic Acid as a Flavorant

A. Artificial Vanilla Flavor

An artificial vanilla flavor was made by mixing the following ingredients.

| Constituent | Parts by Weight |
|---|---|
| Vanillin | 3.5 |
| Ethyl Vanillin | 0.8 |
| Heliotropin | 0.1 |
| Veratraldehyde | 0.5 |
| Benzodihydropyrone | 0.4 |
| Ethanol (95%) | 50.0 |
| Water, distilled | 44.7 |
| Total | 100.0 |

A taste solution was prepared by adding 0.1 g of the above artificial vanilla flavor to a solution of 100 g of sucrose in 900 g of distilled water. To 100 g of the artificial vanilla taste solution was added 0.1 g of a 0.01% solution of 4-isopropyl-3-cyclohexene-1-carboxylic acid in ethanol (0.1 ppm). A bench panel of four tasters compared the treated and untreated taste solutions. All preferred the artificial vanilla containing the additive stating that it was stronger and closer in flavor to a natural vanilla extract.

B. Artificial Cumin Oil

Artificial cumin oil A was prepared by mixing the following ingredients.

| Constituent | Parts by Weight |
|---|---|
| α-Pinene | 1.00 |
| β-Pinene | 16.00 |
| para-Cymene | 13.00 |
| Myrcene | 0.40 |
| gamma-Terpinene | 15.00 |
| Eucalyptol | 0.13 |
| α-Terpineol | 0.20 |
| β-Caryophyllene | 0.05 |
| Bisabolene | 0.02 |
| Cuminyl Alcohol | 2.40 |
| Cuminic Aldehyde | 51.80 |

| Constituent | Parts by Weight |
|---|---|
| Total | 100.00 |

Artificial cumin oil B was prepared by adding 0.1 g of 4-isopropyl-3-cyclohexene-1-carboxylic acid to 9.9 g of artificial cumin oil A. Alcoholic solutions (1%) of artificial cumin oils A and B were prepared by adding 0.1 g of the oil to 9.9 g of 95% alcohol. The 1% alcoholic solutions were separately diluted by adding 0.1 g of each into 100 g of distilled water. A bench panel of four tasters were asked to compare the dilutions. All panelists preferred solution B containing the additive stating that it was more rounded, had more impact, and was more cumin in character than dilution A.

C. Chili Recipe

The following chili concarne recipe was prepared:

| Constituent | Parts by Weight |
|---|---|
| Ground Beef | 1.5 pounds |
| Commercial Onion Soup Mix, Dry | 39 grams |
| Water | 0.5 cup |
| Red Kidney Beans, Canned | 32 ounces |
| Whole Tomatoes, Canned | 32 ounces |
| Cayenne Pepper | 1.0 teaspoon |
| Oregano | 0.5 teaspoon |

The above constituents were mixed and simmered in a covered container for 30 minutes with occasional stirring.

The artificial cumin oils A and B, prepared as in Section B were each mixed into salt (sodium chloride) at a 1% concentration by weight. Each of the above 1% salt mixtures was added to a separate one-cup portion of the above chili recipe and the two portions, one containing artificial cumin oil A and the other containing artificial cumin oil B were compared. The chili containing artificial cumin oil B was preferred in that it was stronger, better blended and more full-bodied in flavor.

D. Commercial Products

The 4-isopropyl-3-cyclohexene-1-carboxylic acid was added to the commercial products listed below in the amount indicated. The products with and without the addition were compared by a bench panel of four tasters. All preferred the samples containing the additive for the reasons indicated.

| Product | PPM of Additive | Comments |
|---|---|---|
| Mixed Vegetable Juice | 0.5 | Spicier, more bite, greater flavor strength |
| Tomato Soup | 0.5 | Rounder, more body |
| Seafood Cocktail Sauce | 1.0 | Spicier, more bite |

E. Tobacco Product

A standard cigarette blend was prepared as described below:

| Constituent | Parts by Weight |
|---|---|
| Bright tobacco | 55 |
| Burley tobacco | 25 |
| Expanded stems | 5 |
| Reconstituted leaf | 15 |
| Total | 100 |

A 0.5% solution of 4-isopropyl-3-cyclohexene-1-carboxylic acid in ethyl alcohol was prepared and injected at amounts of 1, 2 and 3 microliters into 1 g cigarettes made from the above blend. The cigarettes were allowed to equilibrate for 48 hours and then evaluated by smoking as indicated below where the numbers 1, 2 and 3 refer to microliters of solution per gram of cigarette blend. The addition of 1 microliter is equivalent to about 4 ppm.

| Sample | Comments |
|--------|----------|
| 1 | Little or no perceived effect |
| 2 | Improved tobacco flavor; enhancement of mouth feel (fullness) |
| 3 | Much improved tobacco flavor; very smooth, excellent mouth feel; increased moistness of the mouth |

We claim:

1. A fragrance composition comprising an olfactorily effective amount of a compound of the formula

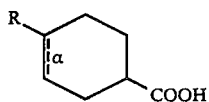

I wherein:
the dotted line designated by α represents an optional bond and
R is an ethyl, propyl or butyl group and at least one other olfactory agent.

2. A composition according to claim 1 wherein 4-isopropyl-3-cyclohexene-1-carboxylic acid was used in preparing said composition.

3. The composition according to claim 2 wherein 4-isopropyl-3-cyclohexene-1-carboxylic acid in substantially pure form was used in preparing said composition.

4. A composition according to claim 1 wherein 4-ethyl-3-cyclohexene-1-carboxylic acid was used in preparing said composition.

5. A composition according to claim 1 wherein 4-isopropylcyclohexane-1-carboxylic acid was used in preparing said composition.

6. A composition according to claim 1 wherein the compound mixture consisting essentially of about 85–95% 4-isopropyl-3-cyclohexene-1-carboxylic acid and about 15–5% 4-isopropylcyclohexane-1-carboxylic acid was used in preparing said composition.

7. A composition according to claim 6 wherein the compound mixture consisting essentially of about 89% 4-isopropyl-3-cyclohexene-1-carboxylic acid and about 11% 4-isopropylcyclohexane-1-carboxylic acid was used in preparing said composition.

8. A method for improving the odor of a fragrance composition which comprises adding thereto an olfactorily effective amount of a compound of the formula

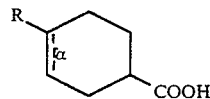

I wherein:
the dotted line designated by α represents an optional bond and
R is an ethyl, propyl, or butyl group.

9. The method of claim 8 wherein 4-isopropyl-3-cyclohexene-1-carboxylic acid is added.

10. The method of claim 9 wherein 4-isopropyl-3-cyclohexene-1-carboxylic acid in substantially pure form is added.

11. The method of claim 8 wherein 4-ethyl-3-cyclohexene-1-carboxylic acid is added.

12. The method of claim 8 wherein the compound mixture consisting essentially of about 85–95% 4-isopropyl-3-cyclohexene-1-carboxylic acid and about 15–5% 4-isopropylcyclohexane-1-carboxylic acid is added.

13. The compound mixture consisting essentially of about 85–95% 4-isopropyl-3-cyclohexene-1-carboxylic acid and about 15% to 5% 4-isopropylcyclohexane-1-carboxylic acid.

14. The composition of claim 13 wherein 4-isopropyl-3-cyclohexene-1-carboxylic acid is about 89% and the 4-isopropylcyclohexane-1-carboxylic acid is about 11%.

15. The compound 4-ethyl-3-cyclohexene-1-carboxylic acid.

16. A tobacco product comprising an effective amount of a compound of the formula

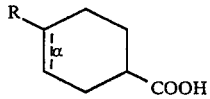

I wherein:
the dotted line designated by α represents an optional bond and
R is an ethyl, propyl or butyl group.

17. A tobacco product according to claim 16 wherein 4-isopropyl-3-cyclohexene-1-carboxylic acid was used to prepare said tobacco product.

18. A tobacco product according to claim 17 wherein 4-isopropyl-3-cyclohexene-1-carboxylic acid in substantially pure form was used to prepare said tobacco product.

19. A tobacco product according to claim 16 wherein 4-ethyl-3-cyclohexene-1-carboxylic acid was used to prepare said tobacco product.

20. A tobacco product according to claim 16 wherein the compound mixture consisting essentially of about 85–95% 4-isopropyl-3-cyclohexene-1-carboxylic acid and about 15–5% 4-isopropylcyclohexane-1-carboxylic acid was used to prepare said tobacco product.

* * * * *